US006656699B2

(12) United States Patent
Pillarisetti et al.

(10) Patent No.: US 6,656,699 B2
(45) Date of Patent: Dec. 2, 2003

(54) METHODS AND COMPOSITIONS FOR GLYCOSIDASE ASSAYS

(75) Inventors: Sivaram Pillarisetti, Norcross, GA (US); Uday Saxena, Atlanta, GA (US); Dongyan Wang, Norcross, GA (US)

(73) Assignee: Reddy US Therapeutics, Inc., Norcross, GA (US)

( * ) Notice: Subject to any disclaimer, the term of this patent is extended or adjusted under 35 U.S.C. 154(b) by 7 days.

(21) Appl. No.: 09/952,648

(22) Filed: Sep. 14, 2001

(65) Prior Publication Data

US 2002/0064806 A1 May 30, 2002

Related U.S. Application Data

(60) Provisional application No. 60/233,075, filed on Sep. 15, 2000.

(51) Int. Cl.[7] .............................. C12Q 1/34; C12Q 1/56; C12Q 1/00; G01N 33/53
(52) U.S. Cl. ................. 435/18; 435/13; 435/4; 435/7.72; 435/7.75; 435/7.1
(58) Field of Search ..................... 435/18, 13, 4, 435/7.72, 7.5, 7.1

(56) References Cited

U.S. PATENT DOCUMENTS

| | | | |
|---|---|---|---|
| 4,859,581 A | 8/1989 | Nicolson et al. | 435/4 |
| 5,968,822 A | 10/1999 | Pecker et al. | 435/232 |
| 6,177,545 B1 | 1/2001 | Pecker et al. | 530/387.1 |
| 6,190,875 B1 | 2/2001 | Ben-Artzi et al. | 435/18 |
| 6,207,402 B1 | 3/2001 | Freeman et al. | 435/180 |
| 6,242,238 B1 | 6/2001 | Freeman et al. | 435/200 |
| 2002/0064806 A1 * | 5/2002 | Pillarisetti et al. | 435/18 |

FOREIGN PATENT DOCUMENTS

| | | |
|---|---|---|
| WO | WO 91/19197 * | 12/1991 |
| WO | WO 98/03638 | 1/1998 |
| WO | WO 99/11798 | 3/1999 |
| WO | WO 99/40207 | 8/1999 |
| WO | WO 99/43830 | 9/1999 |
| WO | WO 99/57153 | 11/1999 |
| WO | WO 00/52178 | 9/2000 |
| WO | WO 00/77241 | 12/2000 |

OTHER PUBLICATIONS

Bartlett, Mark R., et al., "Comparative Analysis of the Ability of Leucocytes, Endothelial Cells and Platelets to Degrade the Subendothelial Basement Membrane: Evidence for Cytokine Dependence and Detection of a Novel Sulfatase", *Immunol. Cell Biol.*, vol. 73, pp. 113–124 (1995).

Dempsey Laurie A., et al., "Heparanase Expression in Invasive Trophoblasts and Acute Vascular Damage", *Glycobiology*, vol. 10, No. 5, pp. 467–475 (2000).

Foxall Carrol, et al., "An Enzyme–Linked Immunoabsorbent Assay Using Biotinylated Heparan Sulfate to Evaluate the Interactions of Heparin–Like Molecules and Basic Fibroblast Growth Factor", *Anal. Biochem.*, vol. 231, No. 2, pp. 366–373 (1995).

Freeman, Craig, et al., "A Rapid Quantitative Assay for the Detection of Mammalian Heparanase Activity", *Biochem. J.*, vol. 325, pp. 229–237 (1997).

(List continued on next page.)

*Primary Examiner*—Louise N. Leary
(74) *Attorney, Agent, or Firm*—Kilpatrick Stockton LLP

(57) ABSTRACT

The present invention is directed to compositions and methods for measuring enzymatic activity, particularly glycosidase activity. Methods of the present invention include assays for quantitatively determining the amount of glycosidase activity in a sample. The present invention also provides methods for the diagnosis of metastatic and inflammatory processes in vitro and in vivo. The present invention further provides compositions and methods for high throughput assays for identifying compounds that effect glycosidase activity.

20 Claims, 7 Drawing Sheets

OTHER PUBLICATIONS

Gallagher, John, T., et al., "Heparan Sulphate–Degrading Endoglycosidase in Liver Plasma Membranes", *Biochem. J.*, vol. 250, No. 3, pp. 719–726 (1988).

Gilat, Dalia, et al., "Molecular Behavior Adapts to Context: Heparanase Functions as an Extracellular Matrix–Degrading Enzyme or as a T Cell Adhesion Molecule, Depending On The Local pH.", *J. Exp. Med.*, vol. 181, No. 5, pp. 1929–1934 (1995).

Goshen, Ran, et al., "Purification and Characterization of Placental Heparanase and its Expression by Cultured Cytotrophoblasts", *Mol. Hum. Reprod.*, vol. 2, No. 9, pp. 679–684 (1996).

Graham, Lloyd D., et al., "Comparison of the Heparanase Enzymes from Mouse Melanoma Cells, Mouse Macrophages, and Human Platelets", *Biochem. Mol. Biol. Int.*, vol. 39, No. 3, pp. 563–571 (1996).

Green, N. Michael, et al., "Avidin", *Adv. in Protein Chemistry, Academic Press*, vol. 29, pp. 85–133 (1975).

Hulett, Mark D., et al., "Cloning of Mammalian Heparanase, an Important Enzyme in Tumor Invasion and Metastasis", *Nat. Med.*, vol. 5, No. 7, pp. 803–809 (1999).

Khan, M.Y, et al., "A Rapid Colorimetric Assay for Heparanase Activity", *Anal. Biochem.*, vol. 196, pp. 373–376 (1991).

Kjellen, Lena, et al., "Proteoglycans: Structures and Interactions", *Annu. Rev. Biochem.*, vol. 60, pp. 443–475 (1991).

Lindahl, Ulf, et al., "Regulated Diversity of Heparan Sulfate", *J. Biol. Chem.*, vol. 273, No. 39, pp. 24979–24982 (1998).

Nakajima, M., et al., "Tumor Metastasis–Associated Heparanase (Heparan Sulfate Endoglycosidase) Activity in Human Melanoma Cells", *Cancer Lett.*, vol. 31, No. 3, pp. 277–283 (1986).

Nakajima, Motowo, et al., "Heparanases and Tumor Metastasis", *J. Cell. Biochem.*, vol. 36, No. 1, pp. 157–167 (1988).

Nakajima, Motowo, et al., "Heparan Sulfate Degradation: Relation to Tumor Invasive and Metastatic Properties of Mouse B16 Melanoma Sublines" *Science*, vol. 220, pp. 611–613 (1983).

Nakajima. Motowo, et al, "Basement Membrane Degradative Enzymes as Possible Markers of Tumor Metastasis", *Cancer Metastasis: Experimental & Clinical Strategies*, pp. 113–122 (1986).

Oosta, Gary M., et al., "Purification and Properties of Human Platelet Heparitinase", *J. Biol. Chem.*, vol. 257, No. 19, pp. 11249–11255 (1982).

Parish, Christopher R., et al., "Treatment of Central Nervous System Inflammation with Inhibitors of Basement Membrane Degradation", *Immunol. Cell Biol.*, vol. 76, pp. 104–113 (1998).

Pillarisetti, Sivaram, et al., "Lysolecithin Induced Alterations of Subendothelial Heparan Sulfate Proteoglycans Increases Monocyte Binding to Matrix", *J.Biol.Chem.*, vol. 270, No. 50, pp. 29760–29765 (1995).

Ricoveri, Walter, et al., "Heparan Sulfate Endoglycosidase and Metastatic Potential in Murine Fibrosarcoma and Melanoma", *Cancer Res.*, vol. 46, No. 8, pp. 3855–3861 (1986).

Rosenberg, Robert D., et al., "Heparan Sulfate Proteoglycans of the Cardiovascular System", *J. Clin. Invest.* vol. 99, No. 9, pp. 2062–2070 (1997).

Vlodavsky, Israel, et al., "Mammalian Heparanase: Gene Cloning, Expression and Function in Tumor Progression and Metastasis", *Nat. Med.*, vol. 5, No. 7, pp. 793–802 (1999).

Vlodavsky, I., et al., "Expression of Heparanase by Platelets and Circulating Cells of the Immune System: Possible Involvement in Diapedesis and Extravasation" *Invasion & Metastasis*, vol. 12, pp. 112–127 (1992).

Wight, Thomas N., "The Extracellular Matrix and Atherosclerosis", *Curr. Opin. Lipidol.* vol. 6, No. 5, pp. 326–334 (1995).

\* cited by examiner

METHODS AND COMPOSITIONS FOR GLYCOSIDASE ASSAYS

RELATED APPLICATION

This application claims priority to U.S. Provisional Application No. 60/233,075 filed Sep. 15, 2000.

TECHNICAL FIELD

This application relates to compositions and methods for measurement of glycosidase activity. Additionally, the present invention provides for compositions and methods for determining metastatic and inflammatory states. The present invention further provides compositions and methods for high throughput assays for compounds that affect glycosidase activity.

BACKGROUND OF THE INVENTION

Proteoglycans (PG) are complex macromolecules present on the cell surfaces and in the extracellular matrices of a wide range of cells (1–3). They are thought to play a major part in chemical signaling between cells. They bind secreted signaling molecules, which can enhance or inhibit the activity of the signaling molecule. Proteoglycans can also bind and regulate the activity of secreted proteins by immobilizing the protein, sterically blocking the activity of the protein, providing a reservoir for delayed release, protecting the protein from proteolytic degradation, or altering the protein for more effective presentation to cell surface receptors.

Proteoglycans are polyanionic substances of high molecular weight and contain many different types of heteropolysaccharide side chains covalently linked to a polypeptide backbone. PG consists of a protein core to which long carbohydrate chains termed glycosaminoglycans (GAG) are covalently attached. GAGs are linear, highly charged polysaccharides composed of a repeating pair of sugars, one of which is always an amino sugar. Formerly, these carbohydrate groups were called mucopolysaccharides, but they are now termed glycosaminoglycans because they can contain derivatives of glucosamine or galactosamine. In principle, proteoglycans have the potential for almost limitless heterogeneity. The underlying repeating pattern of disaccharides in each GAG can be modified by patterns of sulfate groups.

The three major types of GAG found in PG are: 1) hyaluronan (HA), 2) glucosaminoglycans (heparan sulfate (HS), heparin, and keratan sulfate (KS)), and 3) galactosaminoglycans (chondroitin sulfate (CS) and dermatan sulfate (DS)). Approximately 25% of heparan sulfate linear polysaccharides consist of alternating N-acetylated disaccharide units [$\rightarrow$4) $\alpha$-D-GlcNpAc-(1$\rightarrow$4)-$\beta$-D-GlcAp(1$\rightarrow$] and N-sulfated disaccharides $\rightarrow$[4)$\alpha$-D-GlcNpS-(1$\rightarrow$4)-$\beta$-D-GlcAp or $\alpha$-L-IdoAp(1$\rightarrow$]. These polymers are formed by the attachment of a repeating $\rightarrow$[4)$\alpha$-D-GlcNpAc(1$\rightarrow$4)-$\beta$-D-GlcAp(1$\rightarrow$] disaccharide sequence to a serine residue of a core protein through a tetrasaccharide, glucuronosyl-galactosyl-galactosyl-xylosyl, linkage region. This molecule then undergoes partial N-deacetylation followed by N-sulfation of the newly exposed amino groups, followed by partial C-5 epimerization of D-GlcAp to L-IdoAp, and finally O-sulfation. O-sulfates are always found in proximity to N-sulfates, which enhances the clustering of the sulfate residues and the heterogeneity in chemical composition and charge density of heparan sulfate. A typical HS chain consists of a repeating disaccharide unit of hexuronic acid and D-glucosamine. Heparan sulfate proteoglycans are involved in many biological events such as angiogenesis, blood coagulation, cell adhesion, lipid metabolism, tissue morphogenesis, cell differentiation, and regulation of various growth factors and cytokine activities.

Heparan sulfate proteoglycans are important components of the subendothelial extracellular matrix and the basement membrane of blood vessels (2). Basement membranes are continuous sheets of extracellular matrix composed of collagenous and noncollagenous proteins and proteoglycans that separate parenchymal cells from underlying interstitial connective tissue. They have characteristic permeabilities and play a role in maintaining tissue architecture.

In addition to heparan sulfate proteoglycan (HSPG), the basal lamina consists predominantly of a complex network of adhesion proteins, fibronectin, laminin, collagen and vitronectin (6). Heparan sulfate (HS) is an important structural component of the basal lamina. Each of the adhesion proteins interacts with HS side chains of HSPG within the matrix. Thus, HSPG functions as a barrier to the extravasation of metastatic and inflammatory cells. Cleavage of HS by the endoglycosidase heparanase produced by metastatic tumor cells and inflammatory cells destroys the filtering properties of the lamina. In addition, the degradation of the HS may assist in the disassembly of the extracellular matrix and thereby facilitate cell migration (5) by allowing blood borne cells to escape into the bloodstream.

Heparanase activity has been described in a number of tissues and cell types including liver, placenta, platelets, fibroblasts, neutrophils, activated T and B-lymphocytes, monocytes, and endothelial cells (7–16).

No sensitive non-radioactive method is currently available for determination of heparanase activity in tissue or biological fluids. There is currently a need for the development of compositions and methods for simple, rapid, and non-radioactive quantitative assays for the detection of glycosidase activity, particularly heparanase activity. There is also a need for treatments and therapeutic compositions for diseases associated with heparanse activities.

SUMMARY OF THE INVENTION

The present invention is directed to methods for the measurement of cellular activities. Additionally, the present invention comprises compositions and methods for diagnosing diseases, preferably the presence of metastases or neoplastic growth, and for determining the metastatic potential for tumors. The present invention furthers comprises compositions and methods for the diagnosis of inflammatory states in vitro and in vivo.

An aspect of the present invention comprises quantitative measurements of glycosidase activity. A preferred method of the present invention comprises assays for glycosidase activity, more preferably endoglycosidase activity, most preferably determination of heparanase activity. The present invention provides for assays which comprise biotinylated HS bound on streptavidin-coated wells binding additional streptavidin molecules provided in a solution, and this binding is inversely proportional to the extent of digestion of the HS (see FIG. 1). Thus, after digestion by heparanase, HS retains its ability to bind the streptavidin coated in the wells, but HS loses its ability to bind additional streptavidin molecules in solution. By using enzyme-coupled streptavidin, the amount of streptavidin binding biotin-HS following heparanase digestion can be effectively determined, preferably by a color reaction.

The present invention also comprises compositions and methods for screening for compounds that are capable of inhibiting glycosidase activity, preferably heparanase activity. Additionally, the compositions and methods of the present invention may be used in high throughput assays for the identification of compounds capable of inhibiting such enzymatic activity. The present invention also comprises compositions and methods for determining compounds that are capable of inhibiting the metastatic potential of tumors or altered cells and compounds that are capable of inhibiting inflammatory states.

Accordingly, it is an object of the present invention to provide compositions and methods for assays of glycosidase activity that are rapid, simple, and non-radioactive.

Another object of the present invention is to provide compositions and methods for the quantitative measurement of glycosidase activity.

It is another object of the present invention to provide compositions and methods for the measurement of heparanase activity.

Yet another object of the present invention is to provide compositions and methods for screening compounds capable of inhibiting glycosidase activity, particularly heparanase activity.

It is a further object of the present invention to provide compositions and methods for determining the effect of certain compounds on various cellular and enzymatic activities.

It is another object of the present invention to provide compositions and methods for diagnosing the presence of metastases.

Still another object of the present invention is to provide compositions and methods that are useful in determining the metastatic potential of tumors.

Yet another object of the present invention is to provide compositions and methods for determining inflammatory states.

A further object of the present invention is to provide compositions and methods for identifying compounds that are capable of inhibiting the metastases of tumors and compounds that are capable of inhibiting or resolving inflammatory states.

These and other objects, features and advantages of the present invention will become apparent after a review of the following detailed description and claims.

DETAILED DESCRIPTION OF THE INVENTION

Figure 1:
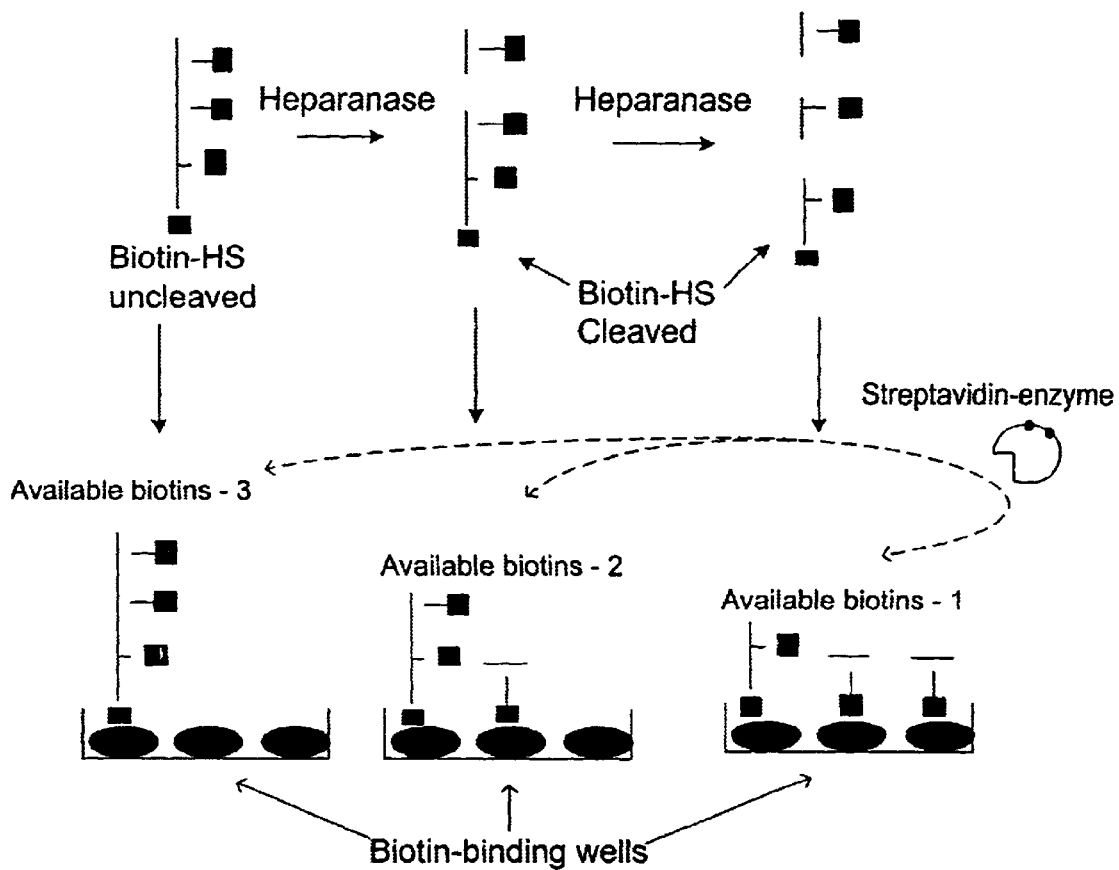
FIG. 1 is a diagram illustrating an assay of heparinase activity.

The present invention may be understood more readily by reference to the following detailed description included herein. Although the present invention herein is described with reference to specific details of certain embodiments thereof, it is not intended that such details should be regarded as limitations upon the scope of the invention. The entire text of the references mentioned herein is hereby incorporated in their entireties by reference.

The present invention is directed to compositions and methods for measurement of cellular and enzymatic activity. The present invention also comprises compositions and methods for the diagnosis of metastases, determination of the metastatic potential of tumors and the determination of the presence of inflammatory states. Additionally, the present invention is directed to compositions and methods for screening for compounds that can alter, preferably inhibit glycosidase activity, particularly heparanase activity, compounds that can alter, preferably inhibit metastases; and compounds that can alter, preferably inhibit, inflammatory reactions and states.

There is increasing interest in heparan sulfate compounds and their related enzymes due to a possible relationship between changes in normal activity and tumor invasiveness and tumor metastatic activity. An important process in tissue invasion by blood-borne tumor cells and white cells involves their passage through the vascular endothelial cell layer and subsequent degradation of the underlying basal lamina or basement membranes and extracellular matrix with a battery of secreted proteases and glycosidases (4,5). Heparanase activity was shown to correlate with the metastatic potential of animal and human tumor cell lines (7, 17–20). It is also known to regulate growth factor activity. Many growth factors remain bound to heparan sulfate in storage form and are disassociated by heparanase during angiogenesis, improving the survival rate of cancer cells.

Serum heparanase levels in rats were higher by more than an order of magnitude after injection of the rats with highly metastatic mammary adenocarcinoma cells. In addition, heparanase activity in the sera of rats bearing MTLn3 tumors correlated well with the extent of the metastases. Moreover, serum/urine heparanase activity in cancer patients was shown to be 2–4 fold increased in particular where tissue metastases were present. Because the cleavage of HS appears to be essential for the passage of metastatic tumor cells and leukocytes through basement membranes, studies of heparanase inhibitors provides the potential of developing a novel and highly selective class of anti-metastatic and anti-inflammatory drugs.

Preferred embodiments of the present invention comprise compositions and methods for the measurement of cellular and enzymatic activities. Such assays can be used to measure such activities, both qualitatively and quantitatively. The assays described herein for determining the presence of such activities may be used in methods for diagnosing metastases, metastatic potential and inflammatory states. The assays of the present invention can also be used to screen for compounds that alter, either stimulate or inhibit, such cellular and enzymatic activities.

A preferred assay is herein described for heparanase activity. Though this assay particularly describes measurement of heparanase activity, it is not intended as a limitation of the invention. The present invention contemplates compositions and methods for assays measuring any glycosidase activity, including, but not limited to, any enzymes with glycosaminoglycan-degrading activity, chondroitinase, heparan sulfate endoglycosidase, heparan sulfate exoglycosidase, polysaccharide lyases, keratanase, hyaluronidase, glucanase, amylase, and other glycosidases and enzymes.

Despite the clinically significant role of heparanase in disease processes, no sensitive high throughput assay to detect heparanase activity is currently available. Existing heparanase assays are cumbersome and time-consuming and require preparation of the radiolabeled substrate and separation of degraded products from the uncleaved substrate (7, 12). Other heparanase assays require the biosynthetic radiolabeling of matrix-associated HSPG and the detection of HS chain degradation by gel-filtration analysis of radiolabeled material released from the matrix (5). These assays unfortunately do not discriminate between protease and heparanase activities. Most heparanase assays also require extensive degradation of the radiolabeled HS (or matrix-derived HSPG) substrate to allow separation of the degraded product from the substrate by gel filtration.

Solid-phase heparanase assays have also been developed where chemically and biosynthetically radiolabeled heparin and HS chains were attached to a solid support, with release of radiolabel from the solid support being a measure of enzyme activity. Such assays, however, suffer from the disadvantage that the immobilized substrate may be less accessible to the heparanase enzyme, and the coupling of the radiolabeled substrate to the solid support, via the substrate's reducing terminus, involves complex protocols. Assays using such procedures are taught in U.S. Pat. No. 4,859,581, which is herein incorporated in its entirety.

Previous studies have also radiolabeled both heparin and HS by iodination at naturally occurring glucosamine residues or by N-acetylation of the partially de-N-sulfated substrate. Such procedures require the use of radioactive iodine, which is a powerful γ emitter and therefore extremely hazardous. A sensitive radioactive assay for heparanase has recently been reported (18). Although the sensitivity of this method (nano units) is comparable to the present method, it requires affinity chromatography of the heparanase-cleaved products on columns of histidine-rich glycoprotein-Sepharose.

There are also some non-radioactive assays available for heparanase. The most used assay for heparanase involves measuring the optical density (at 230 nm) of unsaturated uronic acids formed during degradation of heparin. Apart from that assay's having high sensitivity ($\mu$mols of hexuronic acid), this assay suffers from the disadvantage of interference from certain biological molecules (proteins and nucleic acids), which show strong UV absorption. Another color-based assay for measuring heparanase activity utilizes heparin's ability to interfere with color development during the interaction of protein with the dye Coomassie brilliant blue (25). This assay is relatively specific for heparin, but requires large quantities (up to 600 $\mu$g) of substrate.

The present invention, comprising compositions and methods for assays for enzymatic activity, has advantages over the previously described assays. Such advantages include the relative ease of preparing the substrate, the rapid and simultaneous determination of the presence of enzymatic activity in a large number of samples, and the high sensitivity of such determination of activity. Thus, the methods and compositions of the present invention can be used for diagnostic purposes as well as in screening for compounds that inhibit such activities.

A preferred method of the present invention comprises the following. A composition comprising biotin-HS is mixed with a sample, such as a tumor sample, bodily fluid, or other fluid suspected of having heparinase activity, to form a reaction mixture. This sample may be pretreated to remove contaminating or reactive substances such as endogenous biotin. After incubation, an aliquot or portion of the reaction mixture is removed and placed in a biotin-binding plate. After washing with buffers, a Streptavidin-enzyme conjugate is added to the biotin-binding plate. Reagents for the enzyme are added to form a detectable color product. For example, a decrease in color formation, from a known standard, indicates there was heparinase activity in the sample. The biotin-binding plate comprises any means for binding biotin, preferably to a solid surface.

In general, a preferred method comprises attaching one of a binding partner to a substrate for the enzyme to be measured. Incubation with a sample comprising the enzyme to be measured allows for activity by the enzyme to be measured in a reaction mixture. A portion or the whole reaction mixture, depending on the amount needed, is then mixed with the complementary binding partner, so that the binding partners are bound together. This is the first binding reaction. After incubating to allow for binding, washings are performed. A complementary binding partner, complementary to the first binding partner attached to the substrate, is added. This complementary binding partner may or may not be the same as the first complementary binding partner. This is the second binding reaction. The complementary binding partner in the second binding reaction is labeled in a manner that is detectable. For example, the complementary binding partner is labeled with an enzyme that causes a detectable color change when the appropriate reaction conditions exist.

Preferred methods comprise use of binding partners, including but not limited to, biotin and Streptavidin. Other ways of binding one of the binding partners, such as biotin, can be used at either biotin-binding step, either binding biotin to the plate or in detection of the available biotins. The number of biotins, or other binding partner, that are available for the second binding, is the quantitative result of the assay. "Complementary binding partner" means one of the pair of the binding partners, such as biotin and Streptavidin or an antibody and its antigen. The biotin is the complementary binding partner of Streptavidin, Streptavidin is the complementary binding partner of biotin. An antibody that specifically binds biotin is also a complementary binding partner of biotin.

The enzyme of the sample, for which the activity or presence is being detected, can be any of the enzymes, including but not limited to, any enzymes with glycosaminoglycan-degrading activity, chondroitinase, heparan sulfate endoglycosidase, heparan sulfate exoglycosidase, polysaccharide lyases, keratanase, hyaluronidase, glucanase, amylase, and other glycosidases and enzymes.

The labeled binding partner, in the above method, the enzyme labeled-streptavidin, can be labeled with any detectable marker, including but not limited to, enzymes, dyes, chemiluminescence, and other methods known in the art. A preferred method comprises labeling with an enzyme that produces a color change in its substrate that is detectable. This method is safe, easy, effective and can be used in both qualitative and quantitative methods.

Using the above methods, the amount of enzyme activity in a sample can be determined. Also, the above methods can be used to determine compounds that can inhibit enzyme activity. For example, a composition comprising the compound of interest is added to a known amount of heparinase either before or during the incubation of the heparinase and its substrate-binding partner. If the compound alters the activity of the heparinase, the assay methods of the present invention will show a change in the amount of detectable label. Such assays are used for high throughput determination of the activity of compounds.

The compositions and methods of the present invention can be used to diagnose the presence of metastases, which includes cancer, neoplastic growth, either initial or return metastatic growth. A preferred embodiment of the present invention comprises the following methods. Patients suspected of having one or several tumors, either in an initial finding or in a return of tumor growth, provide a biological sample for testing. This biological sample can be any bodily fluid, tissue, or cellular sample. The biological sample may be pretreated to remove endogenous biotin. The sample is used in the assays of the present invention. An increase in the glycosidase activity, particularly heparanase activity, or a high level of glycosidase activity, is indicative of tumor or metastases presence.

The present invention can be used to measure the metastatic potential of tumors. Tumor tissue or fluid samples are assayed for the presence of glycosidase activity, particularly heparanase activity. Samples are taken once or in sequential biopsies for testing. The transformed cells, such as cancerous or tumor cells, may be found in vivo in living beings, or in vitro, derived from cell lines. A high level of glycosidase activity, or an increase in the amount of glycosidase activity from a baseline determination indicates that the metastatic potential of the tumor or cells is greater than that of normal cells. Other tests known to those skilled in the art can also be used in combination with the assays of the present invention.

The present invention may also be used in determining the presence of inflammatory reactions. An increase in the amount of glycosidase activity, particularly heparanase activity, in a biological sample, is indicative of the presence of an inflammatory reaction. Other tests known to those skilled in the art can also be used in combination with the assays of the present invention.

Another use of the present invention is for determining compounds that influence the glycosidase activity in cells, tissues or whole body responses. Because the present invention comprises assays for quantitatively measuring glycosidase activity, compounds that inhibit or enhance that activity can be determined easily using such assays. For example, once a known amount of heparanase activity is determined from the assays of the present invention, compounds can be added to the assay and the amount of inhibition can be determined. The present invention comprises high throughput assays which can measure the effects on enzyme activity levels by many different compounds. For example, the effect of compounds on the inhibition of glycosidase activity can be measured in vitro or in vivo, using any type of sample known to those skilled in the art.

The present invention is further illustrated by the following examples, which are not to be construed in any way as imposing limitations upon the scope thereof. It will be clear to one of skill in the art that various other modifications, embodiments, and equivalents thereof exist which do not depart from the spirit of the present invention and/or the scope of the appended claims.

EXAMPLES

Example 1
Preparation of Biotinylated HS

Figure 2:
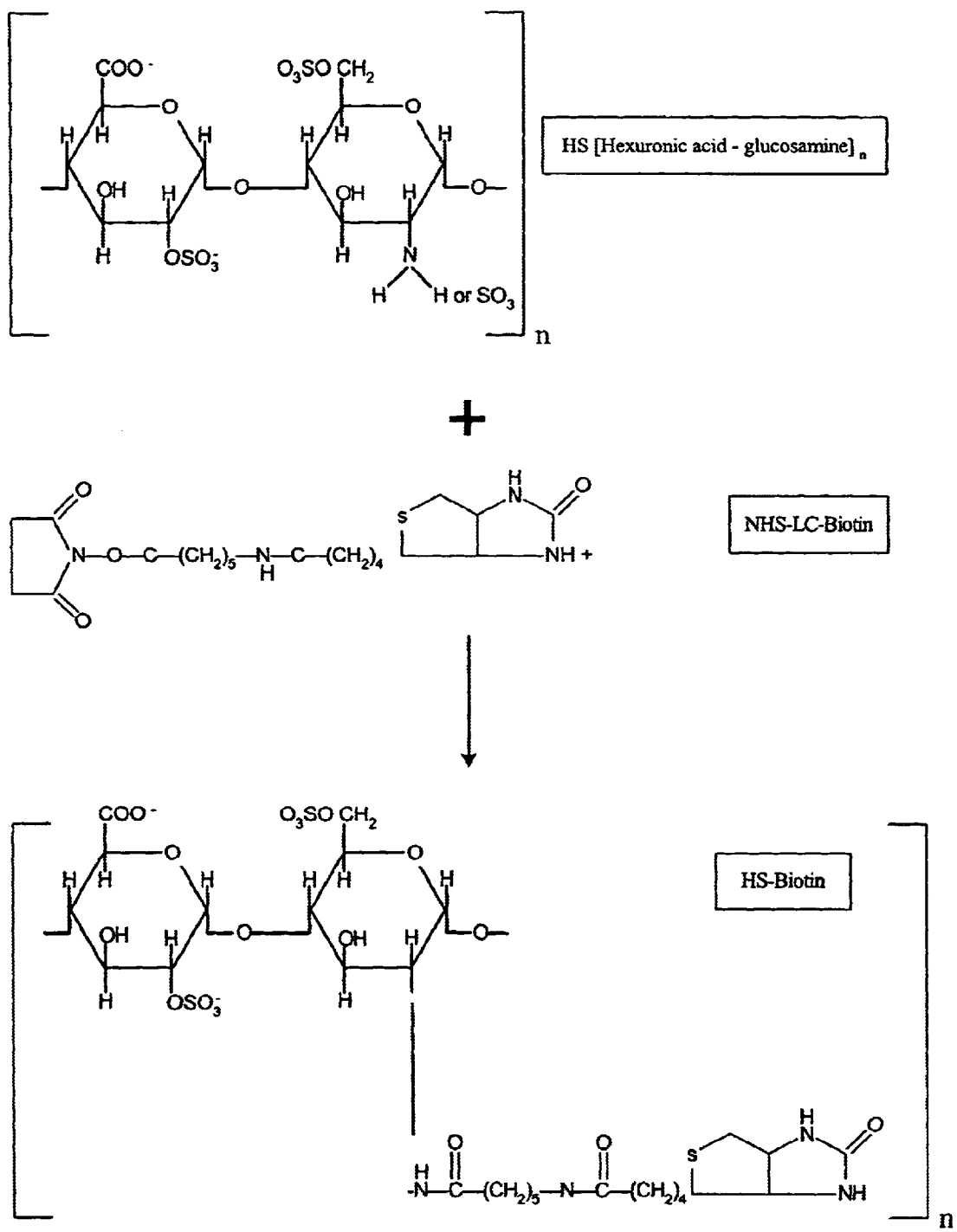
FIG. 2 is a diagram illustrating the linking of biotin to heparan sulfate.

HS was biotinylated using biotin with extended spacer arms using succinimidyl-6-(biotinamido) hexanoate (NHS-LC-Biotin) obtained from Pierce. The chemistry of the reaction between HS and biotin is shown in FIG. 2 and other long chain analogs reduce steric hindrance associated with binding biotinylated molecules to avidin. 0.5 ml HS solution (2 mg/ml in $NaHCO_3$, pH 8.5) was mixed with 0.05 ml of a freshly prepared solution of NHS-LC-Biotin in dimethyl sulfoxide. The mixture was incubated at room temperature for 1 hour. Unconjugated biotin was removed by centrifugation (10,000 RPM) through Microcon-3 filter (Millipore) followed by dilution with phosphate buffered saline (PBS). This procedure was repeated five times to ensure complete removal of free biotin. Unwanted aldehydes in the reaction were then quenched by incubation with one milliliter of Tris-glycine buffer (25 mM-183 mM, pH 8.3) at room temperature for 20 minutes. The mixture was subjected to three rounds of microfiltration as described above. Biotinylated HS (5 mg/ml in PBS) was aliquoted and stored at $-20°$ C. To obtain maximum biotinylation, a 25 fold molar excess biotin was used. Using HABA reagent, it was determined that the ratio of HS to biotin was 1:2.

Example 2
Assessment of Biotinylation

The extent of biotinylation of HS was determined using Avidin-HABA (Pierce Chemical Co) (22). The HABA assay can be used over a wide range of pH and salt concentrations. HABA (4hydroxyazobenzene-2'-carboxylic acid) is a dye that binds to avidin and can serve as an indicator of unoccupied binding sites. Avidin combines stoichiometrically with biotin, making it possible to use any physiochemical differences between avidin and the avidin-biotin complex as the basis of a qualitative and quantitative assay method for either component.

When HABA binds to avidin, there is a large spectral change in the HABA dye. A new absorption band appears at 500 nm, which is characteristic of the quinoid form of the dye. The avidin-biotin complex does not bind HABA and because the dissociation constant of the complex is so low, the dye is stoichiometrically displaced by biotin. Consequently, the HABA assay can be the basis of both calorimetric and titrimetric assays. The amount of avidin can be calculated directly from the increased absorbance at 500 nm, or the dye may be used as an indicator in a spectrophotometric titration with biotin.

The absorption band that results from the avidin-HABA complex decreases proportionately when biotin is added. Since biotin has such a high affinity for avidin, it displaces the HABA dye. The unknown amount of biotin can be determined by preparing a standard curve using known amounts of biotin to displace the HABA which bound to avidin, and plotting against the absorbance at 500 nm.

HABA solution was prepared by adding 24.2 mg of HABA (Pierce) to 9.9 ml $H_2O$, and then adding 0.1 ml 1 M NaOH. Avidin-HABA reagent was prepared by adding 10 mg of avidin and 600 $\mu$l of HABA solution to 19.4 ml of phosphate buffered saline. To 1 ml of Avidin-HABA reagent in a cuvette, 100 $\mu$l of biotinylated HS was added, and the optical density was measured at 500 nm in a spectrophotometer. A standard curve was determined using known amounts of HABA. The decrease in optical density of the HABA following the addition of biotinylated HS was determined.

Example 3
Heparanase Assay

Biotin-labeled HS from Example 1 was digested with heparanase, and the reaction containing undegraded and degraded HS was bound to in a biotin-binding plate (FIG. 1). Streptavidin, conjugated with an enzyme, was added to the binding plate. Quantitation of the color reaction measured the amount of available biotin binding sites. A decrease in color from a known amount reflects HS digestion by heparanase.

A lyophilized powder of heparanase (Heparanase III obtained from Seikagaku) containing 0.1 units of enzymatic activity was hydrated in 100 μl of Reaction Buffer (3.33 mM calcium acetate pH 7.0, containing 0.1 mg/ml BSA). This solution was then diluted to a working concentration of heparanase solution (0.01 micro-units to 1 milli-unit) in Reaction Buffer. Enzyme activity was defined by the manufacturer of the heparanase (Seikagaku) as follows: one unit of enzyme activity is defined as amount required to generate 1 μmole of hexuronic acid per minute. Biotin-HS was diluted to a desired concentration in Reaction Buffer.

To determine heparanase activity, 10 μl of heparanase solution was mixed with 200 μl of the biotin-HS substrate in a 96 well plate. The reaction was incubated at 43° C. for 1 hour. One hundred microliters of the reaction mixture was added to a hydrated biotin-binding plate (Chemicon) and incubated at 37° C., for 30 minutes. The biotin-binding plates were hydrated with 200 μl of 1× Assay Buffer (Chemicon). Wells were washed five times with 1× Assay Buffer and incubated with 100 μl of 1:3000 diluted Streptavidin-Enzyme Conjugate (Chemicon) for 30 minutes at 37° C. The wells were washed five times with 1× Assay Buffer and incubated for 20 minutes with 100 μl of Substrate Solution (Chemicon). Color development in the wells was assessed by measuring the optical density at 450 nm in a microplate reader (Labsystems, Muliskan Ascent model).

Example 4
Assay of Heparanase Activity

Figure 3:
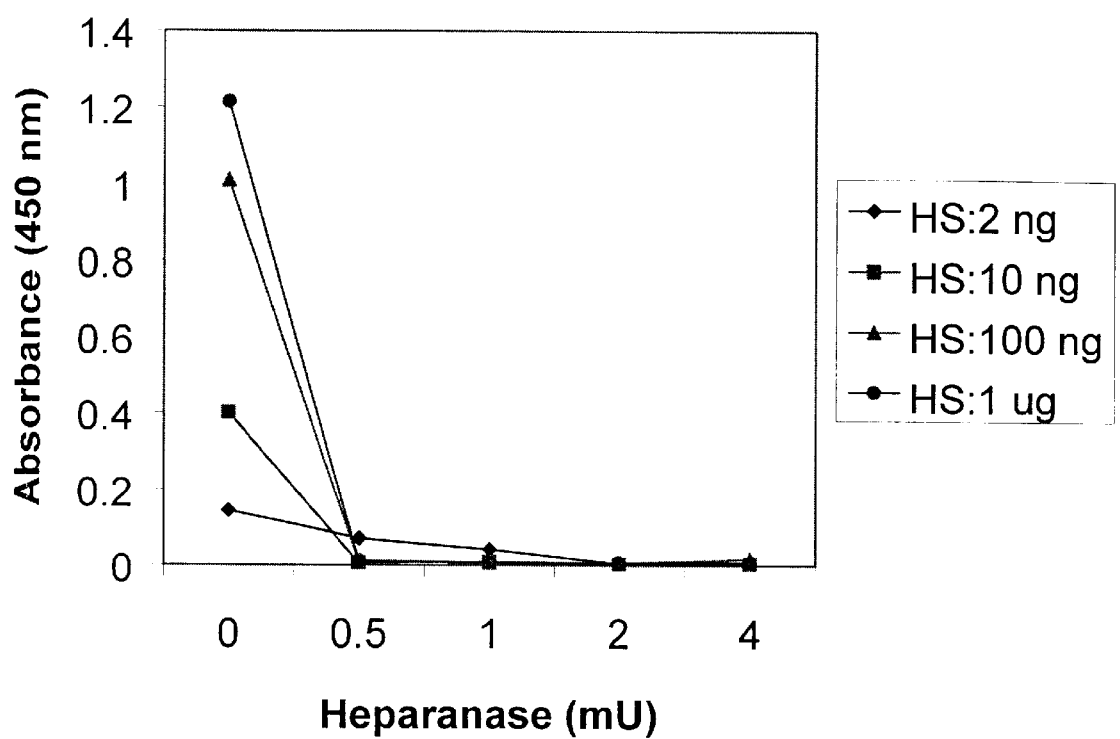
FIG. 3 is a graph showing the measurement of heparanase activity using various amounts of Biotin-HS.

The ability of bacterial heparanase (Seikagaku) to degrade biotin-HS was determined. To determine the optimal amount of HS, different concentrations of biotin-HS were used. These data are presented in FIG. 3. One-half milliunit of heparanase was sufficient to completely digest up to 1 μg of biotin-HS. Biotin-HS was incubated with the indicated amounts of heparitinase for 30 minutes at 37° C. The extent of digestion was determined using streptavidin-enzyme conjugate.

Figure 4:
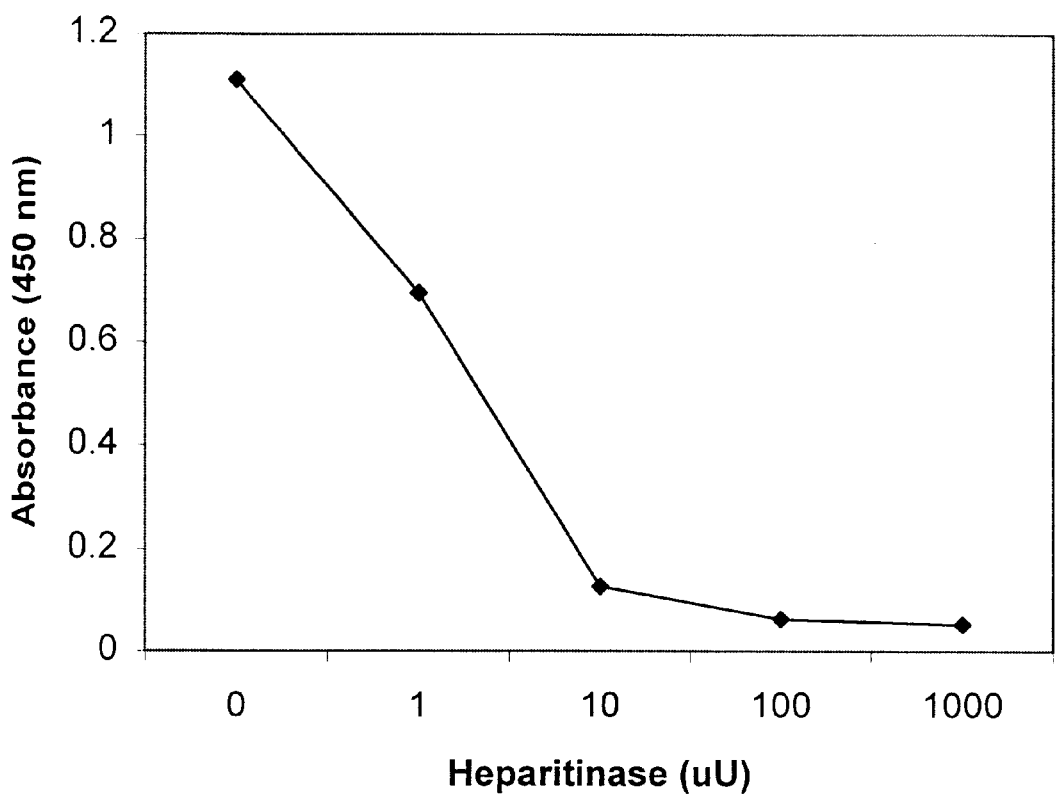
FIG. 4 is a graph showing the digestion of HS by heparanase.

To determine the minimum amount of heparanase required for digestion, 100 ng of biotin HS was digested with various amounts of heparanase. One hundred nanograms of biotin-HS was incubated with the indicated concentrations of heparitinase and the extent of digestion at each concentration was determined using the streptavidin-enzyme conjugate. At this concentration of HS (100 ng), 1 μUnit of heparitinase digested approximately 40% of the initial biotin HS (~40 ng), whereas complete digestion was achieved at 10 μUnits of heparitinase. These data are shown in FIG. 4. At lower substrate concentrations (5–10 ng of HS), heparanase activity in the range of 10–100 nano units could be assayed. This sensitivity is superior to previously described non-radioactive assays and equal or superior to previous radioactivity-based heparanase assays.

Example 5
Specificity of a Heparanase Assay

Figure 5:
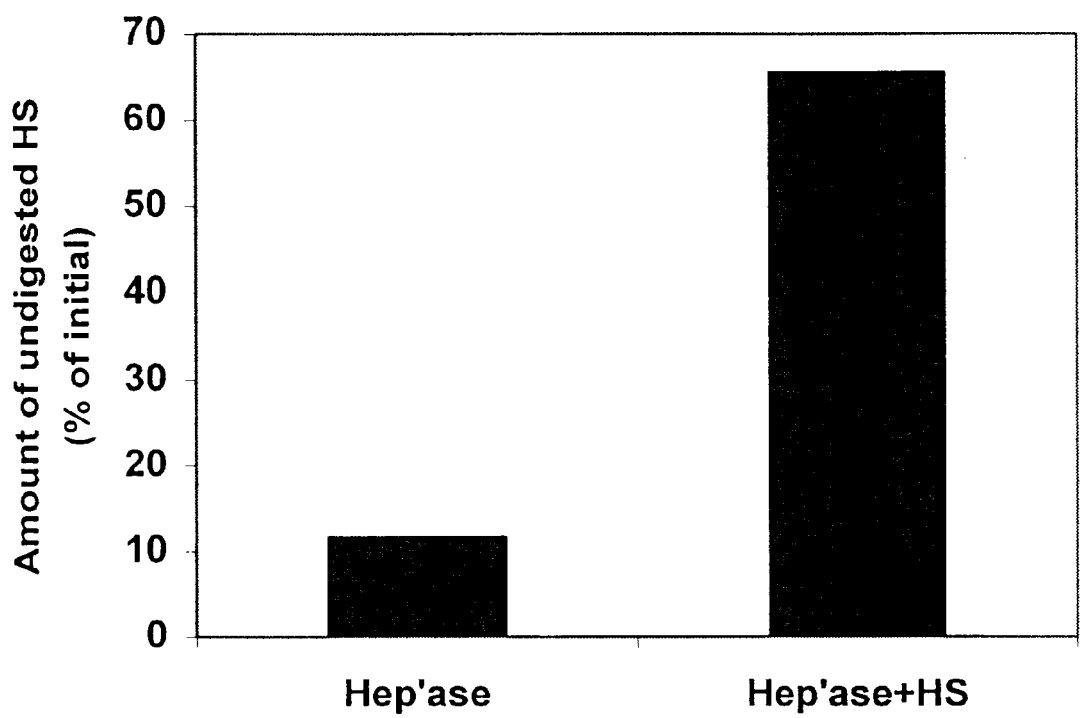
FIG. 5 is a graph showing the substrate specificity of heparanase.

The next step was to determine whether the degradation of HS was specific for HS and heparanase. Biotin-HS digestion was carried out with heparanase in the presence or absence of excess unlabeled HS to determine the specificity of heparanase towards HS. These data are presented in FIG. 5. Heparanase activity toward biotin-HS was inhibited by approximately 60% in the presence of 50 fold (5 μg) excess of unlabeled HS. The biotin-HS degrading activity was specifically due to heparanase.

Example 6
Specificity of Heparanase Assay in the Presence of Proteases

Figure 6:
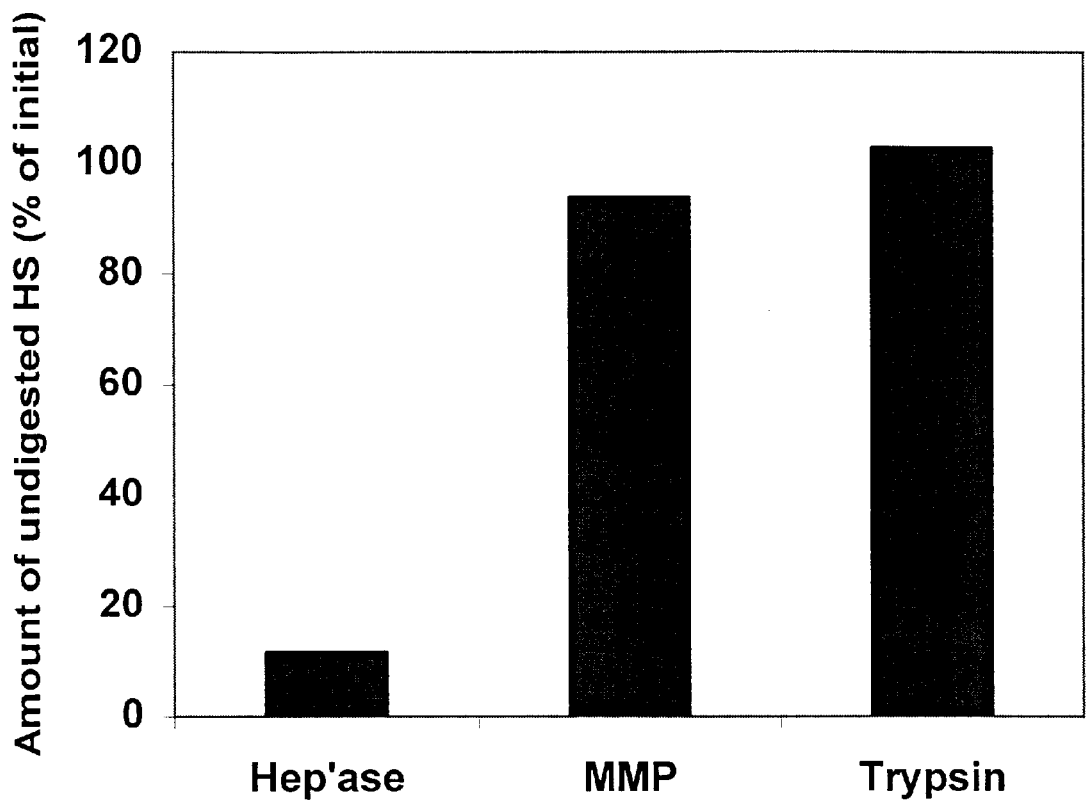
FIG. 6 is a graph showing the specificity of assay in the presence of proteases.

The potential effect of proteases on the heparanase assay is of particular concern because HS contains both a protein core and attached polysaccharide chains. Since biological samples generally contain other degradative enzymes such as proteases, the ability of two different proteases (matrix metalloprotease (MMP-9) and trypsin) to digest biotin-HS was determined. These data are presented in FIG. 6. Neither protease tested (MMP or trypsin) demonstrated any activity that lead to a decrease in the amount of biotin-HS detected by the assay. These data show that the activity that degrades the polysaccharide portion of HS, i.e. the heparanase activity, can be specifically measured in samples such as biological fluids that may contain proteases.

Example 7
Assay of Mammalian Heparanase

The present invention was also used to measure HS degrading activity in mammalian cells. Previously, it was shown that endothelial cells, stimulated with lysolecithin, produce an HS-degrading heparanase activity. This was demonstrated using radiolabeled HS.

Confluent monolayers of endothelial cells were incubated with 50 μM lysolecithin for 24 hours, and conditioned medium and cell lysate were assayed for heparanase activity. Measurement of the level of heparanase activity using the assays of the present invention was as sensitive as using previously known radioactive assays.

Example 8
Heparanase Assay in Serum

Figure 7:
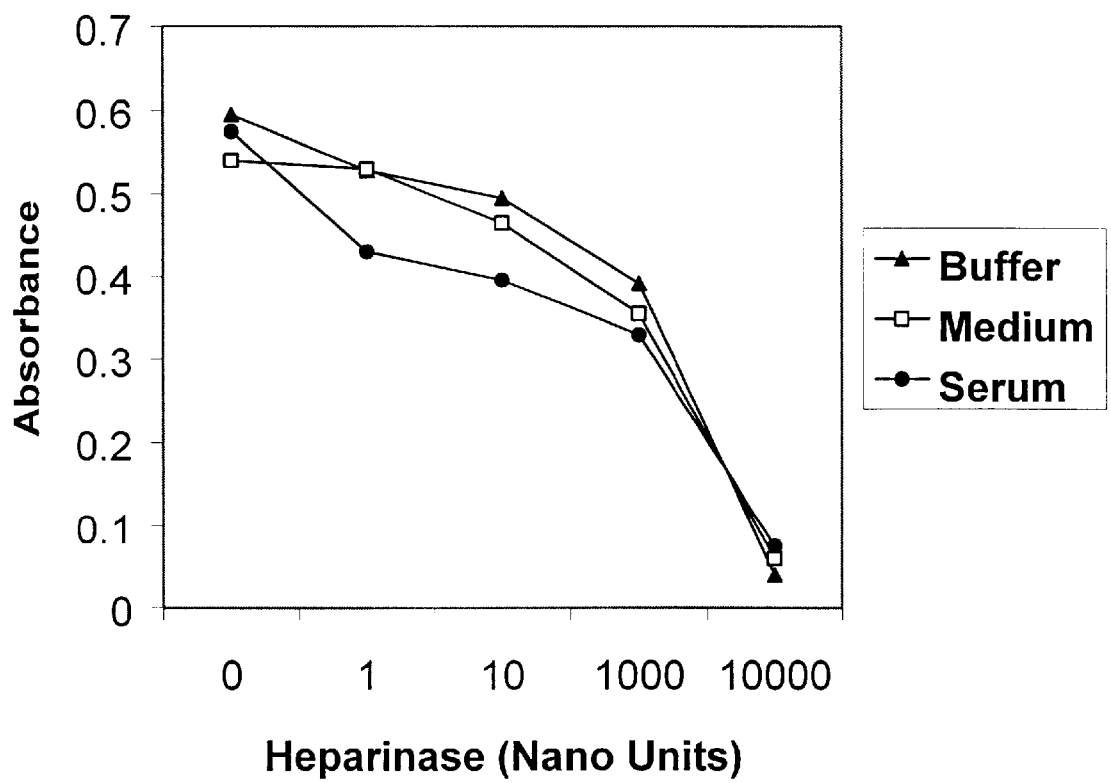
FIG. 7 is a graph showing the measurement of heparanase activity in cell culture media and in serum.

This assay is useful in high-throughput screening that may involve samples containing culture medium or serum. Therefore, the ability to measure heparanase activity in culture medium or serum was determined. Certain culture media and serum may contain endogenous biotin. In order to remove endogenous biotin, serum or culture media was first pre-adsorbed on a streptavidin coated plate. Alternatively, serum or culture media was centrifuge filtered to remove any endogenous biotin. Heparanase was diluted either in Reaction Buffer (3.33 mM calcium acetate pH 7.0, containing 0.1 mg/ml BSA) as a control, culture medium, or serum, and enzyme activity was determined. These data are presented in FIG. 7. Heparanase activity was not affected by the components of culture medium or proteins in serum that remained after the pretreatment to remove endogenous biotin.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

The following references are hereby incorporated by reference in their entirety.

REFERENCES

1. Kjellen, L. and Lindahl, U. (1991) Proteoglycans: structure and interactions. Ann. Rev. Biochem. 60, 443–475

2. Rosenberg, R. D., Shworak N. W., Liu J. Schwartz J. J., and Zhang L. (1997) Heparan sulfate proteoglycans of the cardiovascular system. J. Clin. Invest. 99:2062–70

3. Lindahl, U., Kusche-Gulberg, M., and Kjellen, L. (1998) Regulated diversity of heparan sulfate. J. Biol. Chem. 273, 24979–82

4. Nakajima, M., Irimura, T., Di Ferrante, D., Di Ferrante, N. and Nicolson, G. L. (1983) Heparan sulfate degradation: relation to tumor invasive and metastatic properties of mouse B16 melanoma sublines. Science 220, 611–613

5. Vlodavsky, I., Eldor, A., Haimovitz-Friedman, A., Matzner, Y., Ishai-Michaeli, R., Lider, O., Naparstek, Y., Cohen, I. R. and Fuks, Z. (1992) Expression of heparanase by platelets and circulating cells of the immune system: possible involvement in diapedesis and extravasation. Invasion Metastasis 12, 112–127

6. Wight T. N. (1995) The extracellular matrix and atherosclerosis. Curr Opin Lipidol. 1995 6, 326–34

7. Nakajima, M., Irimura, T. and Nicolson, G. L. (1986) Tumor metastasis-associated heparanase (heparan sulfate endoglycosidase) activity in human melanoma cells. Cancer Lett. 31, 277–283

8. Nakajima, M., Irimura, T. and Nicolson, G. L. (1988) Heparanases and tumor metastasis. J. Cell. Biochem. 36, 157–167

9. Ricoveri, W. and Cappelletti, R. (1986) Heparan sulfate endoglycosidase and metastatic potential in murine fibrosarcoma and melanoma. Cancer Res. 46, 3855–3861

10. Gallagher, J. T., Walker, A., Lyon, M. and Evans, W. H. (1988) Heparan sulphate-degrading endoglycosidase in liver plasma membranes. Biochem. J. 250, 719–726

11. Dempsey L A, Plummer T B, Coombes S L, Platt J L. (2000) Heparanase expression in invasive trophoblasts and acute vascular damage. Glycobiology 10, 467–75.

12. Goshen R, Hochberg A A, Komer G, Levy E, Ishai-Michaeli R, Elkin M, de Groot N, Vlodavsky I. (1996) Purification and characterization of placental heparanase and its expression by cultured cytotrophoblasts. Mol. Hum. Reprod. 2, 679–84.

13. Parish C R, Hindmarsh E J, Bartlett M R, Staykova M A, Cowden W B, Willenborg D. 0. (1998) Treatment of central nervous system inflammation with inhibitors of basement membrane degradation. Immunol Cell Biol. 76, 104–13

14. Gilat, D, Hershkoviz, R, Goldkom, I, Cahalon, L, Komer, G, Vlodavsky, I, Lider, O (1995) Molecular behavior adapts to context: heparanase functions as an extracellular matrix-degrading enzyme or as a T cell adhesion molecule, depending on the local pH. J. Exp. Med. 181, 1929–34

15. Graham, L. D., Underwood, P. A. (1996) Comparison of the heparanase enzymes from mouse melanoma cells, mouse macrophages, and human platelets. Biochem. Mol. Biol. Int. 39, 56371.

16. Pillarisetti, S., Obunike, J. C. and Goldberg, I. J. (1995) Lysolecithin induced alterations of subendothelial heparan sulfate proteoglycans increases monocyte binding to matrix J.Biol.Chem. 270, 29760–29765

17. Nakajima. M, Welch. D. R, Irimura. T, Nicolson. G. L. (1986) Basement membrane degradative enzymes as possible markers of tumor metastasis. Prog Clin Biol Res. 212, 113–22

18. Freeman, C and Parish, C. R. (1997) A rapid quantitative assay for the detection of mammalian heparanase activity Biochem. J. 325, 229–237

19. Vlodavsky, I, Friedmann, Y., Elkin, M., Aingorn, H., Atzmon, R., Ishai-Michaeli, R., Bitan, M., Pappo, O., Peretz, T., Michal, I., Spector, L., Pecker, I. (1999) Mammalian heparanase: gene cloning, expression and function in tumor progression and metastasis. Nat. Med. 5, 793–802

20. Hulett, M. D., Freeman, C., Hamdorf, B. J., Baker, R. T., Harris, M. J. and Parish, C. R. (1999) Cloning of mammalian heparanase, an important enzyme in tumor invasion and metastasis. Nat Med. 5, 803–9

21. Foxall C, Holme K R, Liang W, Wei Z. (1995) An enzyme-linked immunosorbent assay using biotinylated heparan sulfate to evaluate the interactions of heparin-like molecules and basic fibroblast growth factor. Anal. Biochem. 231, 366–73

22. Green, N. M. (1975). Avidin. In: Adv. in Protein Chemistry, Academic Press, New York, 29, 85–133

23. Oosta, G. M., Favreau, L. V., Beeler, D. L. and Rosenberg, R. D. (1982) Purification and properties of human platelet heparitinase J. Biol. Chem. 257, 11249–11255

24. Bartlett, M. R., Underwood, P. A. and Parish, C. R. (1995) Comparative analysis of the ability of leucocytes, endothelial cells and platelets to degrade the subendothelial basement membrane: evidence for cytokine dependence and detection of a novel sulfatase. Immunol. Cell Biol. 73, 113–124

25. Khan, M. Y, Newman, S. A. (1991) A rapid calorimetric assay for heparanase activity Anal. Biochem. 196, 373–6

What is claimed is:

1. A method for detecting glycosidase activity, comprising,
 a) mixing a sample suspected of containing glycosidase activity with a composition comprising a substrate-binding partner to form a reaction mixture;
 b) removing an aliquot of the reaction mixture to a solid substrate comprising a complementary binding partner to bind the substrate-binding partner;
 c) adding a labeled complementary binding partner;
 d) detecting the label; and
 e) determining the amount of glycosidase activity.

2. The method of claim wherein the glycosidase activity is due to the presence of an endoglycosidase.

3. The method of claim 2, wherein the endoglycosidase is heparinase.

4. The method of claim 3, wherein the substrate-binding partner is heparan sulfate-biotin.

5. The method of claim 1, wherein the substrate-binding partner is heparin sulfate-biotin.

6. The method of claim 5, wherein the complementary binding partner is Streptavidin.

7. The method of claim 1, wherein the sample is a bodily fluid.

8. The method of claim 7, wherein the bodily fluid is blood, serum, saliva, tissue fluid, urine, tears or plasma.

9. The method of claim 1, wherein the sample is a tissue sample.

10. The method of claim 9, wherein the tissue sample comprises cells, a biopsy section, a tumor, or neoplasm.

11. A method for detecting compounds that alter a glycosidase, comprising,
 a) mixing a compound with a glycosidase;
 b) adding the mixture of a) with a composition comprising a substrate-binding partner to form a reaction mixture;
 c) removing an aliquot of the reaction mixture to a solid substrate comprising a complementary binding partner to bind the substrate-binding partner;

d) adding a labeled complementary binding partner;

e) detecting the label; and f) determining the change in glycosidase activity.

12. The method of claim 7, wherein the glycosidase is due to the presence of an endoglycosidase.

13. The method of claim 8, wherein the endoglycosidase is heparinase.

14. The method of claim 9, wherein the substrate-binding partner is heparan sulfate-biotin.

15. The method of claim 7, wherein the substrate-binding partner is heparan sulfate-biotin.

16. The method of claim 11, wherein the complementary binding partner is Streptavidin.

17. A method for detecting metastases, comprising, a) mixing a sample from one suspected of having metastases with a composition comprising a substrate-binding partner to form a reaction mixture, wherein the substrate is the substrate for a glycosidase;

b) removing an aliquot of the reaction mixture to a solid substrate comprising a complementary binding partner to bind the substrate-binding partner;

c) adding a labeled complementary binding partner;

d) detecting the label; and e) determining the amount of glycosidase activity.

18. The method of claim 17 wherein the glycosidase is heparinase.

19. The method of claim 17, wherein the substrate-binding partner is heparan sulfate-biotin.

20. The method of claim 5, wherein the complementary binding partner is Streptavidin.

* * * * *